(12) United States Patent
Bagley et al.

(10) Patent No.: US 10,149,716 B2
(45) Date of Patent: Dec. 11, 2018

(54) SELF-SIZING CATHETER FEATURES TO PREVENT OVER-TIGHTENING OF THE ELECTRODE

(71) Applicant: COVIDIEN LP, Mansfield, MA (US)

(72) Inventors: Christopher L. Bagley, Santa Clara, CA (US); Allen D. Jameson, Sunnyvale, CA (US); Hillary K. Huszar, Redwood City, CA (US)

(73) Assignee: COVIDIEN LP, Mansfield, MA (US)

( * ) Notice: Subject to any disclaimer, the term of this patent is extended or adjusted under 35 U.S.C. 154(b) by 452 days.

(21) Appl. No.: 14/925,613

(22) Filed: Oct. 28, 2015

(65) Prior Publication Data

US 2016/0220304 A1 Aug. 4, 2016

Related U.S. Application Data

(60) Provisional application No. 62/110,835, filed on Feb. 2, 2015.

(51) Int. Cl.
*A61B 18/14* (2006.01)
*A61B 18/00* (2006.01)
*A61B 17/00* (2006.01)

(52) U.S. Cl.
CPC ............ *A61B 18/1492* (2013.01); *A61B 2017/00477* (2013.01); *A61B 2018/0022* (2013.01); *A61B 2018/00577* (2013.01)

(58) Field of Classification Search
CPC ....... A61B 18/1492; A61B 2018/0022; A61M 2025/1061; A61M 2025/1084
See application file for complete search history.

(56) References Cited

U.S. PATENT DOCUMENTS

| | | | |
|---|---|---|---|
| 4,740,207 A | 4/1988 | Kreamer | |
| 4,969,890 A | 11/1990 | Sugita et al. | |
| 4,998,539 A | 3/1991 | Delsanti | |
| 5,010,895 A | 4/1991 | Maurer et al. | |

(Continued)

FOREIGN PATENT DOCUMENTS

| | | |
|---|---|---|
| DE | 102013104948 A1 | 11/2014 |
| EP | 1654980 A1 | 10/2006 |

(Continued)

OTHER PUBLICATIONS

Examination Report No. 1 for Application No. 2016200218, dated Nov. 30, 2016, from the Australian Government.

(Continued)

*Primary Examiner* — Michael Peffley (57) ABSTRACT

Methods, apparatuses and systems are described for preventing the over-tightening of a furled ablation structure support around an expandable member. An ablation device for treatment of tissue in body lumens with varying sizes is disclosed. The ablation device may include a catheter, an expansion member coupled with a distal portion of the catheter, and an ablation structure support configured to at least partially unfurl or furl around the expansion member as the expansion member expands or contracts. The ablation device may further include a spacer coupled with the catheter and configured to limit a minimum diameter of the ablation structure support when the expansion member is completely contracted.

20 Claims, 7 Drawing Sheets

(56) References Cited

U.S. PATENT DOCUMENTS

| | | | |
|---|---|---|---|
| 5,192,297 A | 3/1993 | Hull | |
| 5,462,545 A | 10/1995 | Wang et al. | |
| 5,517,989 A | 5/1996 | Frisbie et al. | |
| 5,533,958 A | 7/1996 | Wilk | |
| 5,716,410 A | 2/1998 | Wang et al. | |
| 5,800,334 A | 9/1998 | Wilk | |
| 5,820,629 A | 10/1998 | Cox | |
| 5,836,874 A | 11/1998 | Swanson et al. | |
| 5,846,196 A | 12/1998 | Siekmeyer et al. | |
| 5,997,534 A | 12/1999 | Tu et al. | |
| 6,006,755 A | 12/1999 | Edwards | |
| 6,016,437 A | 1/2000 | Tu et al. | |
| 6,096,054 A | 8/2000 | Wyzgala et al. | |
| 6,102,908 A | 8/2000 | Tu et al. | |
| 6,123,703 A | 9/2000 | Tu et al. | |
| 6,123,718 A | 9/2000 | Tu et al. | |
| 6,152,899 A | 11/2000 | Farley | |
| 6,156,060 A | 12/2000 | Roy | |
| 6,162,184 A | 12/2000 | Swanson | |
| 6,162,237 A | 12/2000 | Chan | |
| 6,179,856 B1 * | 1/2001 | Barbere | A61M 25/1006 604/97.02 |
| 6,254,598 B1 | 7/2001 | Edwards et al. | |
| 6,258,118 B1 | 7/2001 | Baum et al. | |
| 6,551,310 B1 | 4/2003 | Ganz et al. | |
| 6,752,806 B2 | 6/2004 | Durgin et al. | |
| 6,800,083 B2 | 10/2004 | Hiblar et al. | |
| 6,964,661 B2 | 11/2005 | Rioux et al. | |
| 7,150,745 B2 * | 12/2006 | Stern | A61B 18/06 606/41 |
| 8,192,426 B2 | 6/2012 | Stern et al. | |
| 2002/0065542 A1 | 5/2002 | Lax | |
| 2003/0158550 A1 | 8/2003 | Ganz et al. | |
| 2007/0100333 A1 | 5/2007 | Jackson et al. | |
| 2007/0276361 A1 | 11/2007 | Stevens-Wright et al. | |
| 2008/0249464 A1 | 10/2008 | Spencer et al. | |
| 2008/0319350 A1 * | 12/2008 | Wallace | A61B 5/053 600/587 |
| 2009/0024087 A1 * | 1/2009 | Kennedy, II | A61M 25/10 604/99.01 |
| 2009/0093802 A1 | 4/2009 | Kulesa | |
| 2014/0378966 A1 | 12/2014 | Haverkost | |
| 2014/0378967 A1 | 12/2014 | Willard | |
| 2015/0119877 A1 | 4/2015 | Jameson et al. | |
| 2015/0119879 A1 * | 4/2015 | Jameson | A61B 18/1492 606/41 |
| 2015/0119880 A1 | 4/2015 | Huszar et al. | |
| 2015/0119881 A1 | 4/2015 | Bagley et al. | |

FOREIGN PATENT DOCUMENTS

| | | | |
|---|---|---|---|
| EP | 2604212 A1 | 6/2013 | |
| WO | 0128446 A1 | 4/2001 | |
| WO | 2005067668 A2 | 7/2005 | |
| WO | 2008061528 A1 | 5/2008 | |

OTHER PUBLICATIONS

Chinese Office action for Application No. 201610068875.4 dated Oct. 10, 2017, from the Chinese Patent Office.

Notification of the First Office Action from State Intellectual Property Office of the People's Republic of China for Application No. 201510845131.4 dated Aug. 21, 2017.

Extended EP Search Report for Application 15191980.0 from European Patent Office, dated Jun. 14, 2016.

Extended European Search report for Application No. 15202393.3 dated Jun. 22, 2016 from European Patent Office.

Office Action from the Canadian Intellectual Property Office dated Mar. 21, 2017 for Application No. 2,917,513.

* cited by examiner

SELF-SIZING CATHETER FEATURES TO PREVENT OVER-TIGHTENING OF THE ELECTRODE

CROSS REFERENCE TO RELATED APPLICATION

The present application claims the benefit of and priority to U.S. Provisional Application Ser. No. 62/110,835, filed on Feb. 2, 2015, the entire contents of which are incorporated herein by reference.

BACKGROUND

The human body has a number of internal body lumens or cavities located within, such as the differing parts of the gastro-intestinal tract, many of which have an inner lining or layer. Body lumens may include, for example, the esophagus, small and large intestines, stomach, remnant after bariatric surgery, rectum, and anus. These inner linings may be susceptible to disease. In some cases, different ablation techniques have been utilized with respect to the inner lining in order to prevent the spread of disease to otherwise healthy tissue located nearby.

Internal body lumens may have different sizes with respect to each other or with respect to different patients. Therefore, devices may be used that are configured to expand and contract to accommodate a variety of lumen sizes. Typical devices may include a treatment element that wraps around an expandable element such that the treatment element unwraps itself as the expandable element expands and re-wraps itself around the expandable element as the expandable element collapses.

However, devices with wrapped treatment elements may encounter problems during expansion or contraction. For example, for various reasons, the wrapped treatment element may prevent the expandable element from expanding under safe expansion forces.

Therefore, there may be a need for systems, devices, and methods that may overcome the above or other disadvantages of known systems, devices, and methods.

SUMMARY

The described features generally relate to methods, systems, and devices for improving the expansion performance of an expandable treatment device such as an ablation device. Systems may include an expansion member that may be coupled with a catheter. An ablation structure support may be wrapped or furled around the expansion member such that expanding the expansion member may engage body lumens of varying sizes. An over-tightening prevention element such as a spacer may be coupled with the catheter and configured to prevent the ablation structure support from being over-tightened.

In accordance with various embodiments, an ablation device for treatment of tissue in body lumens with varying sizes is provided. The ablation device may include a catheter and an expansion member coupled with a distal portion of the catheter. The expansion member may be a balloon for example. An ablation structure support configured to at least partially unfurl or furl around the expansion member as the expansion member expands or contracts may be included. Furthermore, the ablation device may include a spacer coupled with the catheter and configured to limit a minimum diameter of the ablation structure support when the expansion member is completely contracted.

In some embodiments, the ablation device may further include an elastic member configured to bias the ablation structure support around the expansion member. In such embodiments, the ablation structure support may at least partially overlap itself when the expansion member is completely contracted forming an overlapping portion. Moreover, the expansion member may be expanded by inflating the expansion member with an expansion medium at a pressure sufficient to overcome both an elastic resistance of the elastic member and a frictional resistance caused by the overlapping portion of the ablation structure support. In certain embodiments, the spacer is configured to limit a size of the overlapping portion of the ablation structure support such that the pressure sufficient to overcome both the elastic resistance of the elastic member and the frictional resistance caused by the overlapping portion of the ablation structure support is less than approximately 27.6 kPa.

According to some embodiments, the spacer of the ablation device is configured to limit an outer diameter of the ablation structure support from reducing to less than approximately 11 millimeters when the expansion member is completely contracted. In yet other embodiments, the spacer is configured to maintain a gap between an outer surface of the catheter and an inner diameter of the ablation structure support when the expansion member is completely contracted.

In certain aspects, the spacer is coaxially coupled with the catheter. Moreover, the spacer may comprise one or more O-rings coaxially coupled with the catheter. In some embodiments, the one or more O-rings are made from silicone. According to some embodiments, the spacer comprises a substantially tubular element coaxially coupled with the catheter and extending substantially an entire length of the expansion member.

In accordance with various embodiments, the ablation device may further include an ablation structure coupled with the ablation structure support comprising a plurality of longitudinal electrode zones. In certain aspects, the ablation structure comprises at least one bipolar electrode array. Each of the longitudinal electrode zones may be configured to be selectively enabled or disabled.

According to various embodiments, a method for treatment of tissue in body lumens with varying sizes is provided. The method may include providing an ablation device comprising a catheter, an expansion member coupled with a distal portion of the catheter, an ablation structure coupled with an ablation structure support, wherein the ablation structure support is configured to wrap around the expansion member such that the ablation structure support at least partially unfurls or furls around the expansion member as the expansion member expands or contracts. The method may further include tightening the wrapped ablation structure support around the expansion member while the expansion member is completely contracted, wherein a spacer coupled with the catheter is configured to limit a minimum diameter of the ablation structure support while the wrapped ablation structure support is tightened around the completely contracted expansion member. Additionally, the method may include expanding the expansion member to at least partially unfurl the ablation structure to engage a circumferential section of the body lumen, and delivering energy through the ablation structure to the circumferential section of the body lumen.

In certain embodiments of the method, when the wrapped ablation structure is tightened around the completely contracted expansion member, the spacer is configured to limit an outer diameter of the ablation structure support from reducing to less than approximately 11 millimeters. Moreover, in some embodiments of the method, the ablation device further comprises an elastic member configured to bias the ablation structure support around the expansion member. In such embodiments, when the wrapped ablation structure support is tightened around the completely contracted expansion member, the ablation structure support may at least partially overlap itself forming an overlapping portion. Moreover, in such embodiments, expanding the expansion member may comprise inflating the expansion member with an expansion medium at a pressure sufficient to overcome both an elastic resistance of the elastic member and a frictional resistance caused by the overlapping portion of the ablation structure support.

Furthermore, in some embodiments of the method, the spacer is configured to limit a size of the overlapping portion of the ablation structure support such that the pressure sufficient to overcome both the elastic resistance of the elastic member and the frictional resistance caused by the overlapping portion of the ablation structure support is less than approximately 27.6 kPa.

According to some embodiments, the spacer is coaxially coupled with the catheter. In yet other embodiments, the spacer comprises one or more O-rings coaxially coupled with the catheter. The one or more O-rings may be made from silicone in some embodiments.

Certain embodiments of the present disclosure may include some, all, or none of the above advantages or features. One or more other technical advantages or features may be readily apparent to those skilled in the art from the figures, descriptions, and claims included herein. Moreover, while specific advantages or features have been enumerated above, various embodiments may include all, some, or none of the enumerated advantages or features.

Further scope of the applicability of the described methods and apparatuses will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Methods, systems, and devices are described which may prevent the over-tightening of an expandable treatment device. Systems may include an expansion member coupled with a distal portion of a catheter. An ablation structure support may be wrapped or furled around the expansion member such that expanding the expansion member unfurls the ablation structure support from around the expansion member. Moreover, the ablation structure support may be biased such that it re-furls itself around the expansion member as the expansion member contracts.

A treatment element such as an ablation structure may be coupled with the ablation structure support such that the ablation structure unfurls and furls as the expansion member expands and contracts. The ablation structure may include a flexible circuit capable of wrapping around the expansion member upon which it is disposed. Various aspects of the flexible circuit may be similar to typical integrated circuits and microelectronic devices. The flexible circuit may include multiple separately wired or separately controlled longitudinal electrodes, longitudinal electrode zones, or both.

Furthermore, one or more spacers may be coupled with the catheter to prevent over-tightening of the ablation structure support when the expansion member is completely contracted. In general, the spacers may limit the minimum size of the furled ablation structure support by physically preventing the ablation structure support from being tightened or furled down below a certain threshold. The minimum size of the furled ablation structure support can be measured in terms of its furled diameter, the amount of the ablation structure support that overlaps itself, or the gap distance between the outside surface of the catheter and the inside surface of the ablation structure support.

Figure 1:
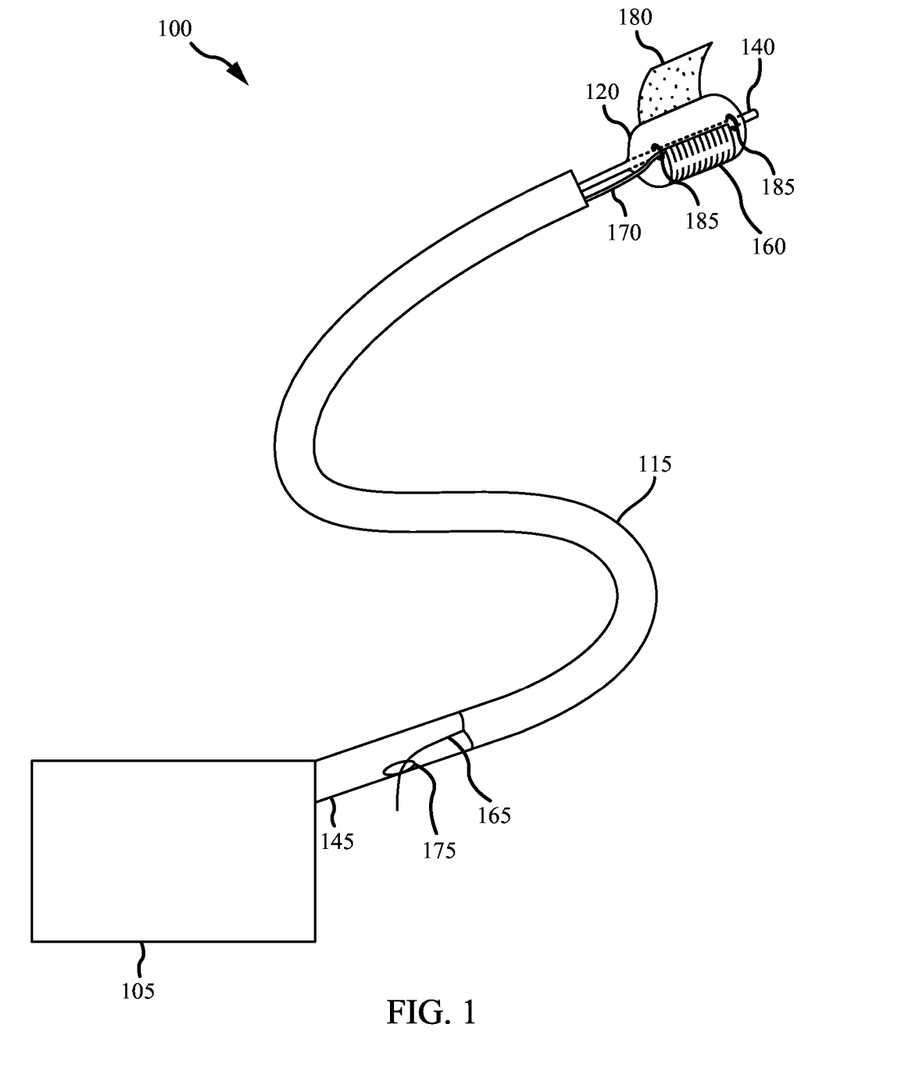
FIG. 1 is a perspective view of a general treatment device in accordance with various embodiments.

With reference to FIG. 1, a perspective view of a general device 100 for delivering treatment to a target treatment area is shown in accordance with various embodiments. The device 100 may be designed for providing treatment to a target area inside of a body, such as the wall of an organ or lumens in the gastrointestinal tract, for example. The device 100 may include a power source 105, a catheter 115, and an expansion member 120. As shown in FIG. 1, the expansion member 120 may be coupled to the catheter 115 near the distal end 140 of the catheter 115. According to some embodiments, the expansion member 120 is an inflatable balloon. The balloon may be made from a compliant, semi-compliant, or non-compliant material.

The expansion member 120 may generally be configured to support an ablation structure support 180 that wraps or furls around the expansion member 120. As described in more detail with reference to FIG. 6, the ablation structure support 180 may include an elastic member that is configured to bias the ablation structure support 180 to wrap around the expansion member 120. Additionally or alternatively, the ablation structure support 180 may be made from a material that is configured to bias itself to furl around the expansion member 120. Furthermore, the ablation structure support 180 may be manually wrapped or furled around the expansion member 120 by an operator of the device 100.

According to various embodiments, an ablation structure 160 is coupled with an outward facing surface of the ablation structure support 180 and may be used to supply therapy to the target treatment site. For example, radio frequency (RF) energy may be delivered to the targeted tissue to provide ablative treatment. In general, the ablation structure 160 is a flexible circuit comprising one or more selectively operable electrodes. Moreover, the selectively operable electrodes may include one or more longitudinal electrodes or longitudinal electrode zones, or both. In certain embodiments, the power source 105 may be configured to selectively operate these one or more longitudinal electrodes or electrode zones via the plurality of transmission lines 170 connecting the power source 105 to the ablation structure 160. The feature of the ablation structure 160 comprising multiple selectively operable electrode zones and the associated circuitry is described in more detail in co-owned U.S. application Ser. Nos. 14/519,409, 14/519,950, and 14/520,028, each of which are incorporated herein by reference for all purposes.

Since the ablation structure 160 is flexible and coupled with the ablation structure support 180, the ablation structure support 180 and the ablation structure 160 may be configured to at least partially unfurl or furl around the expansion member 120 as the expansion member 120 expands or contracts. Therefore, the device 100 may expand and contract to treat tissue in body lumens with varying sizes.

In general, the device 100 may operate by positioning a guide assembly 165 inside a body and passing the expansion member 120 over the guide assembly 165 such that the expansion member 120 may be delivered to a target treatment site inside the body. The power source 105 may then be used to supply power to the ablation structure 160 disposed on the expansion member 120 so that therapy may be applied to the target treatment site. The power source 105 may also include an expansion or inflation source such as a pump that delivers an expansion medium to the expansion member 120 at a controlled pressure. Alternatively, the expansion source or pump may be a separate component (not shown) from the power source 105.

In accordance with various embodiments, the treatment device 100 also includes one or more spacers 185 coupled with the catheter 115. The one or more spacers 185 may be configured to limit a minimum diameter of the ablation structure support 180 when the expansion member 120 is completely contracted or unexpanded. Additionally or alternatively, the one or more spacers 185 may be configured to limit the amount of overlap of the ablation structure support 180 when the expansion member 120 is completely contracted. According to yet other embodiments, the one or more spacers 185 are configured to maintain a gap between the outer surface of the catheter 115 and the inner surface of the furled ablation structure support 180 when the expansion member 120 is completely contracted. As shown in FIG. 1, the spacers 185 may be coupled with the catheter 115 and positioned within the expansion member 120. As described in more detail with reference to FIGS. 3-5, the one or more spacers 185 may include one or more O-rings, one or more substantially tubular elements, or one or more O-rings with multiple radially protruding spokes.

Figure 2A:
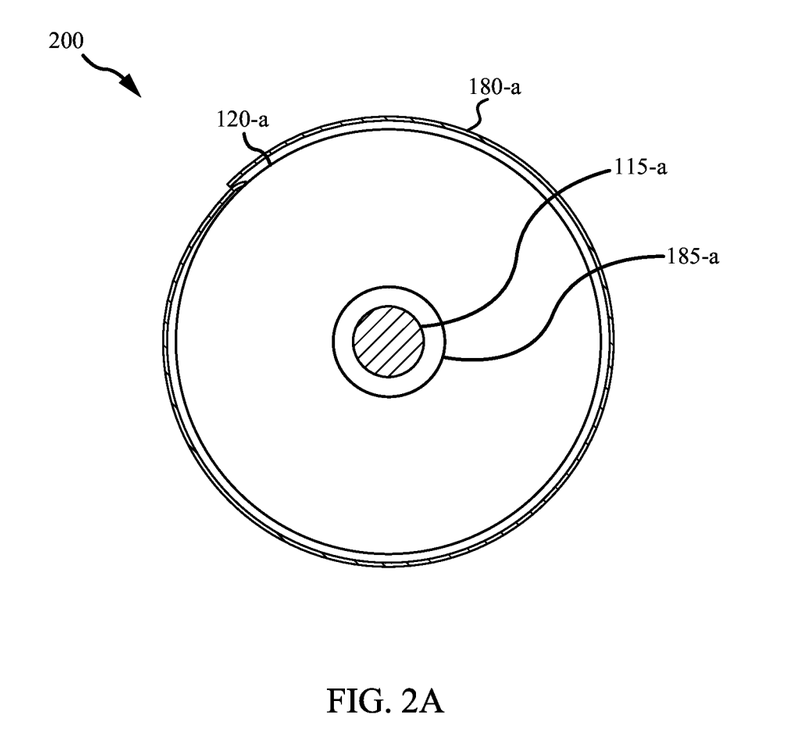
FIG. 2A is a cross-sectional view of an ablation device shown in a fully expanded configuration in accordance with various embodiments.

With reference to FIG. 2A, a cross-sectional view of an ablation device 200 is shown in a fully expanded configuration in accordance with various embodiments. Ablation device 200 may be an example of the device 100 described in connection with FIG. 1. The ablation device 200 includes an expansion member 120-*a* and an ablation structure support 180-*a* configured to at least partially furl and unfurl around the expansion member 120-*a* as the expansion member 120-*a* expands and contracts. Additionally, the expansion member 120-*a* is coupled with a catheter 115-*a*. Although not shown in FIG. 2A or 2B for clarity, an ablation structure, such as ablation structure 160 described with reference to FIG. 1, may be coupled with an outward facing surface of the ablation structure support 180-*a*.

The ablation device 200 also includes one or more spacers 185-*a* coupled with the catheter 115-*a* according to various embodiments. As shown, the one or more spacers 185-*a* may be coaxially coupled with the catheter 115-*a*. As described in more detail with reference to FIGS. 3-5, the one or more spacers 185-*a* may comprise one or more O-rings, elongated tubular members, or O-rings with radially protruding spokes.

Figure 2B:
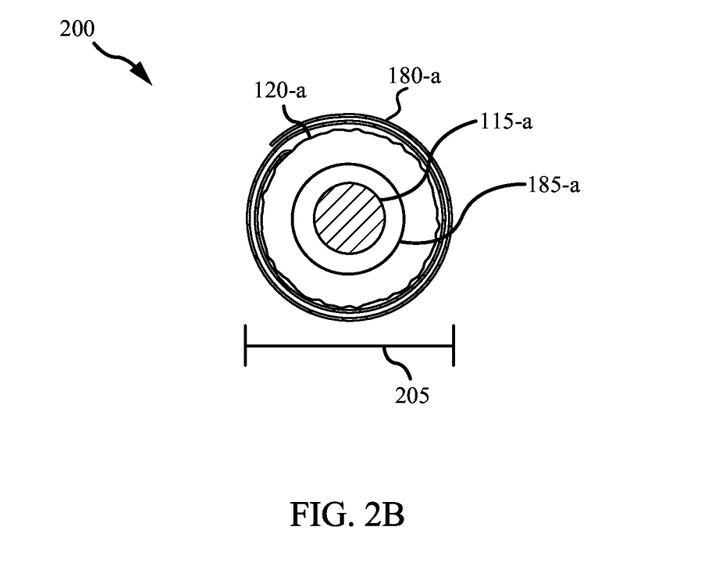
FIG. 2B is a cross-sectional view of an ablation device shown in a partially expanded configuration in accordance with various embodiments.

Turning to FIG. 2B, a cross-sectional view of the ablation device 200 is shown in a partially expanded configuration. As shown, the expansion member 120-*a* is less expanded in FIG. 2B than it is in the fully expanded configuration illustrated in FIG. 2A. The ablation device 200 may contract from its fully expanded configuration by deflating the expansion member 120-*a*. As described in more detail with respect to FIG. 6, an elastic element may bias the ablation structure support 180-*a* to wrap or furl around the expansion member 120-*a* as the expansion member 120-*a* is deflated or otherwise contracted. Additionally, an operator may assist in the furling of the ablation structure support 180-*a* by manually furling or tightening the ablation structure support 180-*a* around the expansion member 120-*a*. In either case, as the ablation structure support 180-*a* is further furled around the expansion member 120-*a*, the outer diameter 205 of the furled ablation structure support 180-*a* reduces. In accordance with various embodiments, once the expansion member 120-*a* is completely contracted or deflated, the inside surface of the expansion member 120-*a* will come into contact with the outer surface of the one or more spacers 185-*a* and the furled ablation structure support 180-*a* will not be able to tighten down any further. Accordingly, the one or more spacers 185-*a* may be configured to maintain a gap between the outer surface of the catheter 115-*a* and the inner diameter of the furled ablation structure support 180-*a* when the expansion member 120-*a* is completely contracted. In particular, the magnitude of this gap is equal to the thickness of the spacer 185-*a* and the thickness of the expansion member 120-*a*.

Once the expansion member 120-*a* is fully contracted or deflated, the outer diameter 205 of the furled ablation structure support 180-*a* will be at its minimum. Accordingly, the one or more spacers 185-*a* may be configured to limit the minimum diameter 205 of the ablation structure support 180-*a* when the expansion member 120-*a* is completely contracted. In some embodiments, the spacers 185-*a* are configured to prevent the outer diameter 205 of the furled ablation structure support 180-*a* from reducing below approximately 11 millimeters when the expansion member 120-*a* is completely contracted.

Moreover, as shown in FIG. 2B, as the ablation structure support 180-*a* is furled around the expansion member 120-*a*, the ablation structure support 180-*a* may overlap itself forming an overlapping portion. It may be appreciated that the size of the overlapping portion will increase as the ablation structure support 180-*a* continues to furl around the expansion member 120-*a*. Accordingly, when the expansion member 120-*a* is fully contracted or deflated, the size of the overlapping portion will be at a maximum. Due to the overlapping portion of the ablation structure support 180-*a*, there exists a frictional force between the layers of overlapping material. The magnitude of this frictional force depends at least in part on the size of the overlapping portion, the frictional characteristics of the material used for the ablation structure support 180-*a*, and the existence of any lubrication between the layers of the ablation structure support 180-*a*.

To expand the ablation device 200 from a completely collapsed configuration, the expansion member 120-*a* is expanded or inflated thereby causing the ablation structure support 180-*a* to unfurl from around the expansion member 120-*a*. According to some embodiments, the expansion member 120-*a* is inflated with a gas or liquid at a controlled inflation pressure. In such embodiments, the inflation pressure must be sufficiently high to overcome the resistance provided by the expansion member 120-*a* itself and/or the resistance provided by the furled ablation structure support 180-*a*. The total of all the forces opposing expansion of the expansion member 120-*a* may be referred to as the expansion resistance. The resistance provided by the furled ablation structure support 180-*a* may include at least the frictional resistance caused by the overlapping portion in addition to any elastic resistance caused by either an attached elastic member or the inherent elastic behavior of the ablation structure support 180-*a* material. As discussed above, the magnitude of the frictional force depends on the amount of overlap of the ablation structure support 180-*a* and the coefficient of friction between the layers of overlapping portion. Moreover, as discussed in more detail with reference to FIG. 6, the magnitude of the elastic resistance of the furled ablation structure support 180-*a* due to an elastic element depends on the type, number, and configuration of elastic elements.

When the expansion member 120-*a* is being expanded within a body lumen, the magnitude of the inflation pressure must be limited due to safety concerns associated with over-inflation. Therefore, in accordance with various embodiments, the total expansion resistance of the ablation structure support 180-*a* may be limited such that the ablation structure support 180-*a* can unfurl at inflation pressures at or below the prescribed safe maximum inflation pressure. The maximum safe inflation pressure may vary according to the particular application, but in some embodiments, the maximum safe inflation pressure is approximately 27.6 kPa (4 psi). According to some embodiments, the total expansion resistance may be reduced by reducing the frictional resistance caused by the overlapping portion of the ablation structure support 180-*a*. Therefore, the spacers 185-*a* may be configured to limit a size of the overlapping portion of the ablation structure support 180-*a* such that the inflation pressure sufficient to overcome both the elastic resistance of the elastic member and a frictional resistance caused by the overlapping portion of the ablation structure support 180-*a* remains below the safe maximum inflation pressure.

Figure 3:
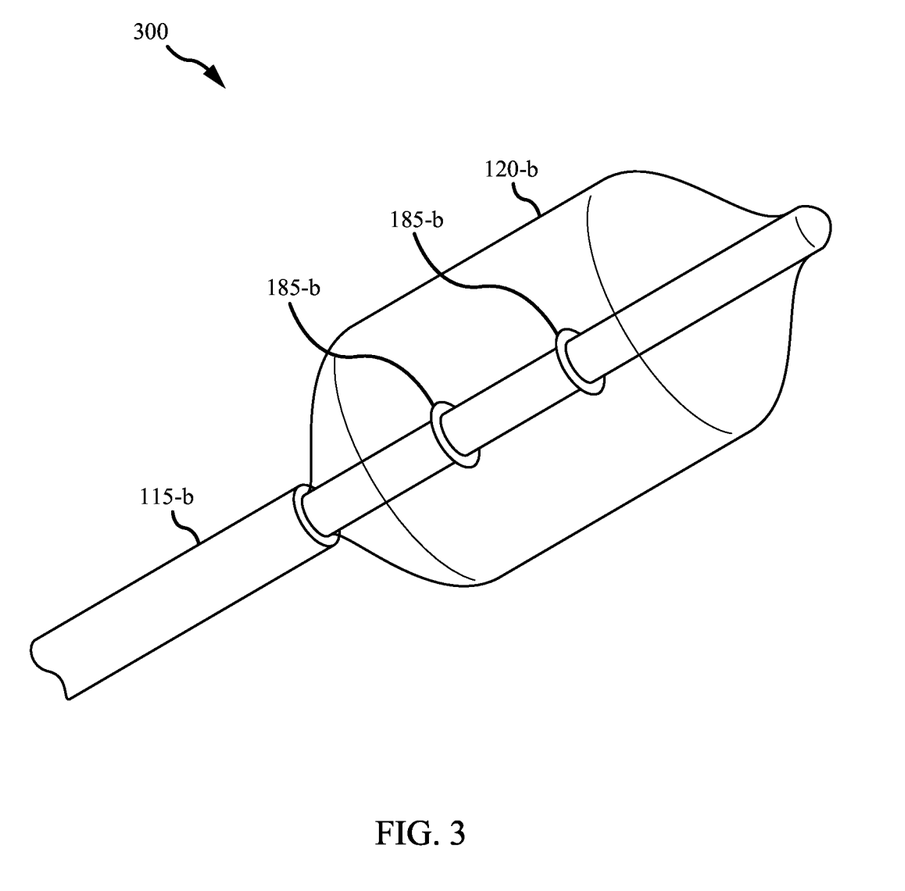
FIG. 3 is a perspective view of an ablation device shown in a fully expanded configuration in accordance with various embodiments.

With reference to FIG. 3, a perspective view of an ablation device 300 is shown in an expanded configuration in accordance with various embodiments. The ablation device 300 may be an example of the ablation devices 100 or 200 described in connection with FIGS. 1-2. Accordingly, ablation device 300 includes an expansion member 120-*b* coupled with a distal end of a catheter 115-*b*. Although not shown in FIG. 3 for clarity, ablation device 300 may include an ablation structure support (e.g., ablation structure support 180 or 180-*a*) and an ablation structure (e.g., ablation structure 160 and 160-*a*) coupled with an outer surface of the expansion member 120-*b* and configured to at least partially furl or unfurl as the expansion member 120-*b* expands and contracts.

In addition, the ablation device 300 includes one or more spacers 185-*b*, which may be examples of the spacers 185, 185-*a* described in connection with FIGS. 1-2. In particular, as shown in FIG. 3, the spacers 185-*b* may comprise two O-rings that are coaxially mounted to the catheter 115-*b*. In accordance with some embodiments, the O-rings 185-*b* are made from silicone. However, it may be appreciated that a variety of materials may be used for the O-rings 185-*b* such as plastic or rubber. The O-rings 185-*b* may be attached to the catheter 115-*b* by selecting O-rings 185-*b* with an inner diameter that fits snuggly around the outer surface of the catheter 115-*b*. Adhesives may also be used to affix the O-rings 185-*b* in place along the catheter 115-*b*. Although two O-rings 185-*b* are illustrated in FIG. 3, it may be appreciated that any number of O-rings 185-*b* may be used. For example, in some embodiments, three or more O-rings 185-*b* are used.

In accordance with various embodiments, the outer diameter of the O-rings 185-*b* may be selected to prevent the over-tightening of the ablation structure support (not shown for clarity) as described with reference to FIGS. 1-2. In particular, the outer diameter of the O-rings 185-*b* may be selected such that the minimum outer diameter of the furled ablation structure support is limited when the expansion member 120-*b* is completely contracted. In a particular embodiment, the outer diameter of the ablation structure support is limited to approximately 11 millimeters by the O-rings 185-*b* when the expansion member 120-*b* is completely contracted. In accordance with other embodiments, the O-rings 185-*b* may be selected such that the amount of overlap of the ablation structure support is limited when the expansion member 120-*b* is completely contracted. For example, the O-rings 185-*b* may limit the amount of overlap of the ablation structure support such that the inflation pressure sufficient to overcome the frictional resistance caused by the overlapping portion and all other expansion resistances is less than a maximum safe inflation pressure. In accordance with various embodiments, the maximum safe inflation pressure is approximately 27.6 kPa (4 psi). Furthermore, the outer diameter of the O-rings 185-*b* may be selected to maintain a gap of a certain size between the outer surface of the catheter 115-*b* and the inside surface of the ablation structure support to prevent over-tightening of the ablation structure support when the expansion member 120-*b* is completely contracted.

Figure 4:
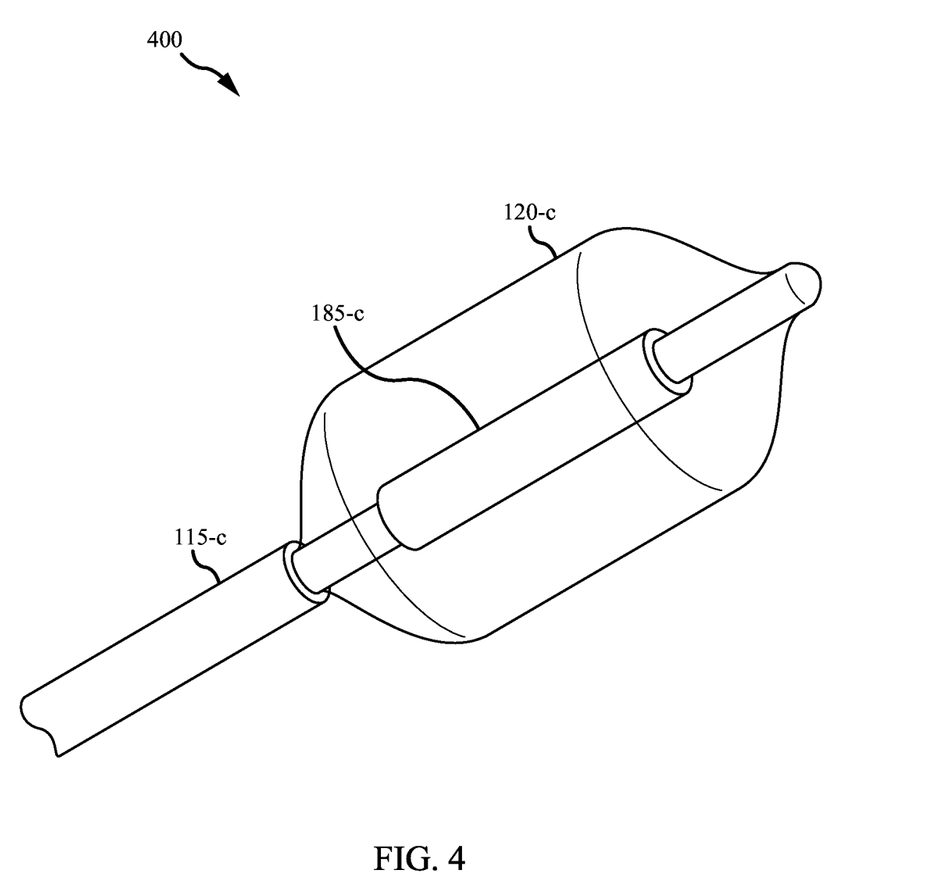
FIG. 4 is a perspective view of an ablation device shown in a fully expanded configuration in accordance with various embodiments.

With reference to FIG. 4, a perspective view of an ablation device 400 is shown in an expanded configuration in accordance with various embodiments. The ablation device 400 may be an example of the ablation devices 100, 200 described in connection with FIGS. 1-2. Accordingly, the ablation device 400 includes an expansion member 120-*c* coupled with a distal portion of a catheter 115-*c*. Although not shown in FIG. 4 for clarity, the ablation device 400 may include an ablation structure support (e.g., ablation structure support 180 or 180-*a*) and an ablation structure (e.g., ablation structure 160 and 160-*a*) coupled with an outer surface of the expansion member 120-*c* and configured to at least partially furl or unfurl as the expansion member 120-*c* expands and contracts. Moreover, the ablation device 400 includes one or more spacers 185-*c*, which may be an example of the spacers 185, 185-*a* described with reference to FIGS. 1-2.

As shown, the spacer 185-*c* comprises a tubular element coaxially coupled with the catheter 115-*c*. Similar to the O-rings 185-*b* described with reference to FIG. 3, the tubular element 185-*c* may be coupled with the catheter 115-*c* by snuggly fitting the tubular element 185-*c* over the outer surface of the catheter 115-*c*. In some embodiments, the tubular element 185-*c* extends substantially along the entire length of the expansion member 120-*c*. However, in other embodiments the tubular element 185-*c* extends only a partial length of the expansion member 120-*c*. Moreover, in some embodiments multiple substantially tubular members 185-*c* may be used. The tubular member 185-*c* may be made from any suitable material, such as silicone, plastic, or rubber.

As described with reference to FIGS. 1-2, the spacer 185-*c* may be configured to prevent the over-tightening of the furled ablation structure support (not shown for clarity). For example, the outer diameter of the tubular member 185-*c* may be selected such that the minimum outer diameter of the furled ablation structure support is limited when the expansion member 120-*c* is completely contracted. According to some embodiments, the outer diameter of the ablation structure support is limited to approximately 11 millimeters by the tubular member 185-*c* when the expansion member 120-*c* is completely contracted. In other embodiments, the tubular member 185-*c* is selected such that the amount of overlap of the ablation structure support is limited when the expansion member 120-*c* is completely contracted. For example, the tubular member 185-*c* may limit the amount of overlap of the ablation structure support such that the inflation pressure sufficient to overcome the frictional resistance caused by the overlapping portion and all other expansion resistances is less than a maximum safe inflation pressure. In a particular embodiment, the maximum safe inflation pressure is approximately 27.6 kPa (4 psi).

Figure 5:
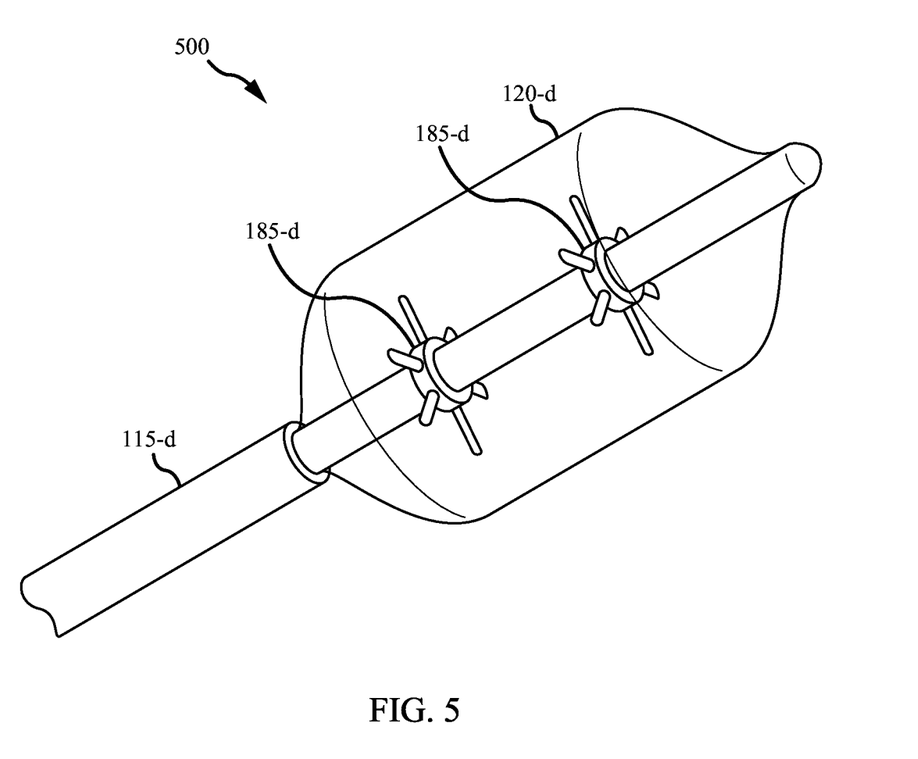
FIG. 5 is a perspective view of an ablation device shown in a fully expanded configuration in accordance with various embodiments.

With reference to FIG. 5, a perspective view of an ablation device 500 is shown in an expanded view in accordance with various embodiments. The ablation device 500 may be an example of the ablation devices 100, 200 described in connection with FIGS. 1-2. Accordingly, the ablation device 500 may include an expansion member 120-*d* coupled with a distal end of a catheter 115-*d*. Although not shown in FIG. 5 for clarity, the ablation device 500 may include an ablation structure support (e.g., ablation structure support 180 or 180-*a*) and an ablation structure (e.g., ablation structure 160 and 160-*a*) coupled with an outer surface of the expansion member 120-*d* and configured to at least partially furl or unfurl as the expansion member 120-*d* expands and contracts. Additionally, the ablation device 500 may include spacers 185-*d*.

As shown in FIG. 5, the spacers 185-*d* may comprise hubs with several radially protruding spokes. The over-tightening prevent elements 185-*d* may be affixed to the catheter 115-*d* in a similar fashion as described with reference to FIGS. 3-4. Moreover, although two spacers 185-*d* are shown, it may be appreciated that any number of spacers 185-*d* may be used.

The several radially protruding spokes of the spacers 185-*d* form an effective outer diameter of the spacers 185-*d*. Thus, in a similar fashion as described with reference to FIGS. 1-4, the diameter of the spacers 185-*d* may be selected to prevent the over tightening of the furled ablation structure support.

Figure 6:
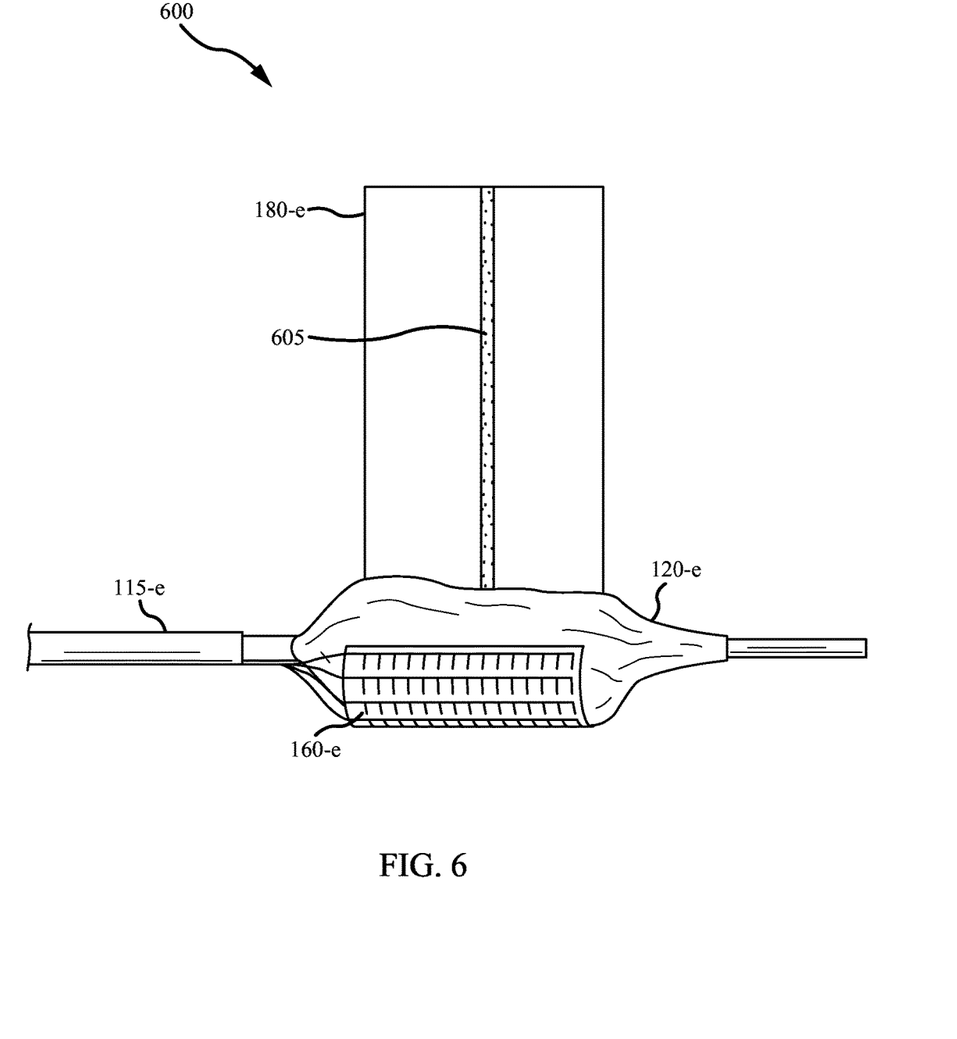
FIG. 6 is a perspective view of an ablation device shown in a partially expanded configuration in accordance with various embodiments.

With reference to FIG. 6, a perspective view of an ablation device 600 is shown in a partially expanded configuration in accordance with various embodiments. The ablation device 600 may be an example of any ablation device described in connection with FIGS. 1-5. Accordingly, the ablation device 600 may include an expansion member 120-*e* coupled with a distal portion of a catheter 115-*e*. Moreover, an ablation structure support 180-*e* may be coupled with an outside surface of the expansion member 120-*e* and configured to at least partially furl or unfurl as the expansion member 120-*e* expands and contracts. An ablation structure 160-*e* may be coupled with an outward facing surface of the ablation structure support 180-*e* and also configured to furl and unfurl around the expansion member 120-*e*.

In accordance with various embodiments, the ablation device 600 includes an elastic member 605 that may be configured to bias the ablation structure support 180-*e* around the expansion member 120-*e*. In some embodiments, the elastic member 605 is a spring or a spring-like element with elastic deformation characteristics. Moreover, although the elastic element 605 is shown extending a full length of the ablation structure support 180-*e*, in other embodiments, the elastic element 605 only extends a partial length of the ablation structure support 180-*e*. Furthermore, although only a single elastic element 605 is illustrated, in some embodiments, multiple elastic elements 605 are used with either equal or unequal sizes. It may be appreciated that the one or more elastic elements 605 provide an elastic resistance to the expansion of expansion member 120-*e* that must be overcome for the expansion member 120-*e* to expand. The magnitude of this elastic resistance depends on the type of material used for the one or more elastic elements 605, and the number, size, and orientation of the elastic elements 605. The feature of using spring-like elements 605 to bias the ablation structure support 180-*e* around the expansion member 120-*e* is more fully described in co-owned U.S. application Ser. Nos. 14/519,409, 14/519,950, and 14/520,028, each of which are incorporated herein by reference for all purposes.

Figure 7:
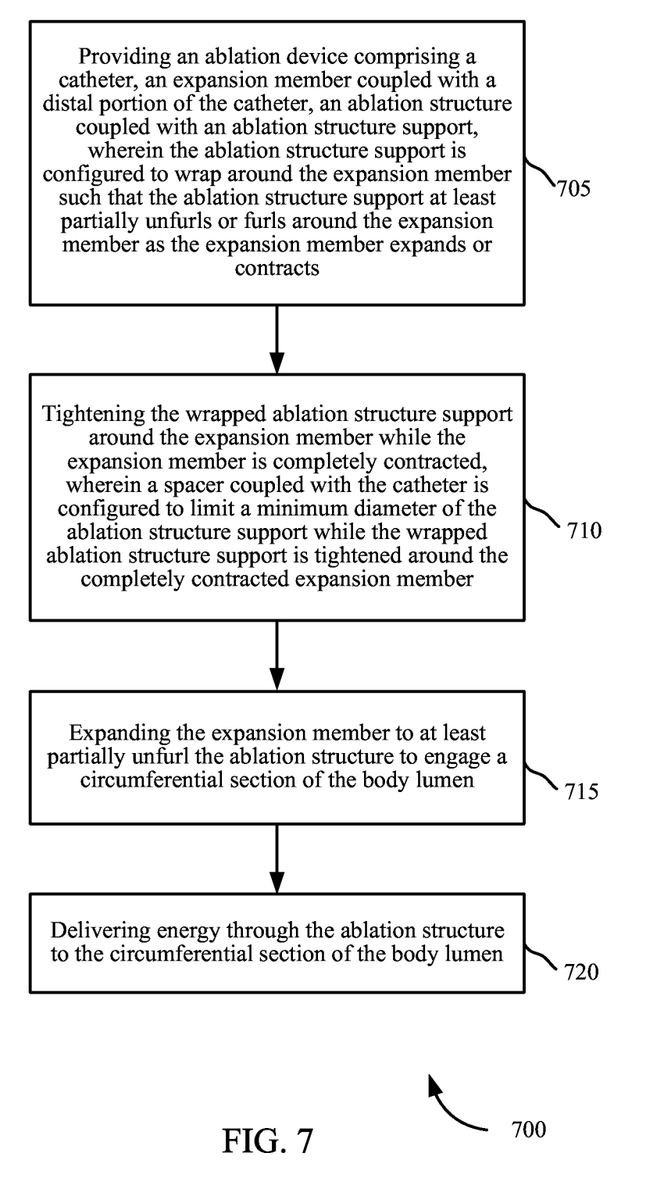
FIG. 7 is a flow diagram of a method for treating tissue in body lumens with varying sizes in accordance with various embodiments.

With reference to FIG. 7, a flow diagram of a method 700 for treating tissue in body lumens with varying sizes is described in accordance with various embodiments. The method 700 may include, at step 705 providing an ablation device 100 comprising a catheter 115, an expansion member 120 coupled with a distal portion of the catheter 115, an ablation structure 160 coupled with an ablation structure support 180, wherein the ablation structure support 180 is configured to wrap around the expansion member 120 such that the ablation structure support 180 at least partially unfurls or furls around the expansion member 120 as the expansion member 120 expands or contracts. Step 705 of method 700 may be implemented with any of the ablation devices 100, 200, 300, 400, 500, or 600 described with reference to any of FIGS. 1-6.

Furthermore, at step 710, the method 700 may include tightening the wrapped ablation structure support 180 around the expansion member 120 while the expansion member 120 is completely contracted, wherein a spacer 185 coupled with the catheter 115 is configured to limit a minimum diameter 205 of the ablation structure support 180 while the wrapped ablation structure support 180 is tightened around the completely contracted expansion member 120. As discussed above, the tightening of the wrapped ablation structure support 180 may occur naturally as the expansion member 120 is contracted due to a biasing effect of an elastic member 605 and/or due to the manual tightening or wrapping of the ablation structure support 180 by an operator of the ablation device. Moreover, as described with reference to FIGS. 1-5, the spacer 185 may take the form of one or more O-rings, or a substantially tubular member, or a hub with multiple radially protruding spokes.

At step 715, method 700 may further include expanding the expansion member 120 to at least partially unfurl the ablation structure 160 to engage a circumferential section of the body lumen. In accordance with some embodiments, expanding the expansion member 120 may include inflating the expansion member 120 with an inflation medium such as gas or liquid at a controlled inflation pressure.

Moreover, method 700 may further include, at step 720, delivering energy through the ablation structure 160 to the circumferential section of the body lumen. As described in connection with FIG. 1, delivering energy through the ablation structure 160 may include delivering energy from a power source 105.

In accordance with various embodiments, when the wrapped ablation structure support 180 is tightened around the completely contracted expansion member 120, the spacer 185 may be configured to limit an outer diameter 205 of the ablation structure support 180 from reducing to less than approximately 11 millimeters.

Additionally, as described above, in various embodiments an ablation device further includes an elastic member 605 configured to bias the ablation structure support 180 around the expansion member 120. Furthermore, according to various embodiments described with reference to FIGS. 2A-2B, when the wrapped ablation structure support 180 is tightened around the completely contracted expansion member 120, the ablation structure support 180 at least partially overlaps itself forming an overlapping portion. Accordingly, expanding the expansion member 120 may include inflating the expansion member 120 with an expansion medium at a pressure sufficient to overcome both an elastic resistance of the elastic member 605 and a frictional resistance caused by the overlapping portion of the ablation structure support 180. In such embodiments, the spacer 185 may be configured to limit a size of the overlapping portion of the ablation structure support such that the pressure sufficient to overcome both the elastic resistance of the elastic member 605 and the frictional resistance caused by the overlapping portion of the ablation structure support 180 is less than approximately 27.6 kPa (4 psi).

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

The invention claimed is:

1. An ablation device for treatment of tissue in body lumens with varying sizes comprising:
a catheter;
a balloon member coupled with a distal portion of the catheter, wherein the balloon member is configured to be inflated up to a maximum inflation pressure;
an electrode structure support configured to at least partially unfurl or furl around the balloon member as the balloon member expands or contracts, wherein the electrode structure support forms an overlapping portion at least when the balloon member is completely deflated; and
a spacer coupled with the catheter and configured to limit a size of the overlapping portion such that an inflation pressure sufficient to overcome a frictional resistance caused by the overlapping portion of the electrode structure support remains below the maximum inflation pressure while the balloon member is inflated.

2. The ablation device of claim 1, further comprising an elastic member configured to bias the electrode structure support around the balloon member, and wherein:
the balloon member is expanded by inflating the balloon member with an expansion medium at a pressure sufficient to overcome both an elastic resistance of the elastic member and the frictional resistance caused by the overlapping portion of the electrode structure support.

3. The ablation device of claim 2, wherein the spacer is configured to limit a size of the overlapping portion of the electrode structure support such that the pressure sufficient to overcome both the elastic resistance of the elastic member and the frictional resistance caused by the overlapping portion of the electrode structure support is less than approximately 27.6 kPa.

4. The ablation device of claim 1, wherein the spacer is configured to limit an outer diameter of the electrode structure support from reducing to less than approximately 11 millimeters when the balloon member is completely deflated.

5. The ablation device of claim 1, wherein the spacer is configured to maintain a gap between an outer surface of the catheter and an inner diameter of the electrode structure support when the balloon member is completely deflated.

6. The ablation device of claim 1, wherein the spacer is coaxially coupled with the catheter.

7. The ablation device of claim 1, wherein the spacer comprises one or more O-rings coaxially coupled with the catheter.

8. The ablation device of claim 7, wherein the one or more O-rings comprise silicone.

9. The ablation device of claim 1, wherein the spacer comprises a substantially tubular element coaxially coupled with the catheter and extending substantially an entire length of the balloon member.

10. The ablation device of claim 1, further comprising an electrode structure coupled with the electrode structure support comprising a plurality of longitudinal electrode zones.

11. The ablation device of claim 10, wherein the electrode structure comprises at least one bipolar electrode array.

12. The ablation device of claim 10, wherein each of the longitudinal electrode zones is configured to be selectively enabled or disabled.

13. The ablation device of claim 1, wherein the balloon member comprises a balloon.

14. A method for treatment of tissue in body lumens with varying sizes comprising:
providing an ablation device comprising a catheter, a balloon member coupled with a distal portion of the catheter, wherein the balloon member is configured to be inflated up to a maximum inflation pressure, an electrode structure coupled with an electrode structure support, wherein the electrode structure support is configured to wrap around the balloon member such that the electrode structure support at least partially unfurls or furls around the balloon member as the balloon member expands or contracts;

tightening the wrapped electrode structure support around the balloon member such that the electrode structure support forms an overlapping portion at least while the balloon member is completely deflated, wherein a spacer coupled with the catheter is configured to limit a size of the overlapping portion such that an inflation pressure sufficient to overcome a frictional resistance caused by the overlapping portion of the electrode structure support remains below the maximum inflation pressure while the balloon member is inflated;

expanding the balloon member to at least partially unfurl the electrode structure to engage a circumferential section of a body lumen; and delivering energy through the electrode structure to the circumferential section of the body lumen.

15. The method of claim 14, wherein when the wrapped electrode structure support is tightened around the completely deflated balloon member, the spacer is configured to limit an outer diameter of the electrode structure support from reducing to less than approximately 11 millimeters.

16. The method of claim 14, wherein the ablation device further comprises an elastic member configured to bias the electrode structure support around the balloon member, and wherein:

expanding the balloon member comprises inflating the balloon member with an expansion medium at a pressure sufficient to overcome both an elastic resistance of the elastic member and the frictional resistance caused by the overlapping portion of the electrode structure support.

17. The method of claim 16, wherein the spacer is configured to limit a size of the overlapping portion of the electrode structure support such that the pressure sufficient to overcome both the elastic resistance of the elastic member and the frictional resistance caused by the overlapping portion of the electrode structure support is less than approximately 27.6 kPa.

18. The ablation device of claim 14, wherein the spacer is coaxially coupled with the catheter.

19. The ablation device of claim 14, wherein the spacer comprises one or more O-rings coaxially coupled with the catheter.

20. The ablation device of claim 19, wherein the one or more O-rings comprise silicone.

* * * * *